United States Patent [19]

Kamin

[11] Patent Number: 4,700,580
[45] Date of Patent: Oct. 20, 1987

[54] AVIATION FUEL TESTER

[76] Inventor: Paul N. Kamin, Town St., W Cornwall, Conn. 06796

[21] Appl. No.: 831,871

[22] Filed: Feb. 24, 1986

[51] Int. Cl.⁴ .......................................... G01N 1/10
[52] U.S. Cl. ............................ 73/864.51; 73/61.1 R
[58] Field of Search .......... 73/864.51, 863.85, 863.86, 73/61.1 R, 306, 319, 864.91

[56] References Cited

U.S. PATENT DOCUMENTS

| 1,344,663 | 6/1920 | Waldrep | 73/306 |
| 3,011,349 | 12/1961 | Kratz | 73/863.86 |
| 3,198,016 | 8/1965 | Poorman | 73/863.86 |
| 3,411,343 | 11/1968 | Baird, Jr. | 73/864.91 X |
| 3,976,572 | 8/1976 | Reick | 73/61.1 R |
| 4,289,027 | 9/1981 | Gleaves et al. | 73/863.86 X |
| 4,524,811 | 6/1985 | Taylor | 73/864.51 X |
| 4,549,440 | 10/1985 | Fournier et al. | 73/863.86 X |
| 4,580,453 | 4/1986 | Taylor | 73/863.85 X |
| 4,610,171 | 9/1986 | Nason | 73/864.91 X |

FOREIGN PATENT DOCUMENTS 2071846 9/1981 United Kingdom ............ 73/863.86

Primary Examiner—Stewart J. Levy
Assistant Examiner—Tom Noland
Attorney, Agent, or Firm—Peter R. Bahn

[57] ABSTRACT

A clear plastic device for the sampling of aviation fuel to allow visual inspection for contaminants that may be contained therein. The hand-held device operates in a "groove" mode or a "prong" mode for different fuel tank quick-release valves. A float inside the device allows visualization of the position of a gasoline-water interface.

4 Claims, 2 Drawing Figures

AVIATION FUEL TESTER

FIELD OF INVENTION

This invention fits into the category of being a hand-held device for sampling aviation fuel for visualization of any contaminants contained therein.

BACKGROUND OF THE INVENTION

An important safety procedure in the operation of single engine airplanes is pre-flight sampling and inspection of the aviation fuel from the aircraft fuel tanks. Various contaminants may have compromised the integrity of the aviation fuel. One such contaminant is water that may have been contributed by the condensation of moisture on various parts of the fuel tank.

To facilitate rapid sampling of aviation fuel, single engine aircraft typically possess quick-release valves on the underside of their wing fuel tanks. These valves are of two types, a circular valve that may be conveniently depressed by a prong shaped object, and a wing valve that may be depressed by an appropriately indented or grooved object.

One tool which facilitates the rapid sampling of aviation fuel from single engine airplanes is disclosed in U.S. Pat. No. 3,011,349 for a Composite Tool and Receptacle by Kratz.

The present invention constitutes an improvement over the Kratz tool in the following respects: The present invention operates in both the "prong" mode and the "groove" mode to catch a falling sample of fuel while simultaneously depressing the quick-release valve of a fuel tank. The Kratz tool operates in this simultaneous fashion only for the "prong" mode.

The Kratz tool also has a sharp pointed object sticking out from the body of the fuel receptacle, thereby making it awkward and dangerous to carry about in one's pocket. The present invention, in the "groove" mode, has no exposed sharp objects, and so may be conveniently and safely carried about in the user's pocket.

Finally, the Kratz tool does not contain a float which would help to quickly identify the position of a gasoline-water interface. If the Kratz tool did have a float, it is contructed in such a way that the float would probably be poured out of the receptacle when the fuel sample was discarded, thereby getting lost. The present invention does have a float for easy identification of the position of the gasoline-water interface. The construction of the present invention also makes it impossible for the float to be accidentally discarded with the fuel sample, by virtue of the fact that said float is physically trapped inside the fuel receptacle.

DESCRIPTION OF THE INVENTION

One embodiment of the present invention is displayed in FIG. 1 and FIG. 2.

Figure 1:
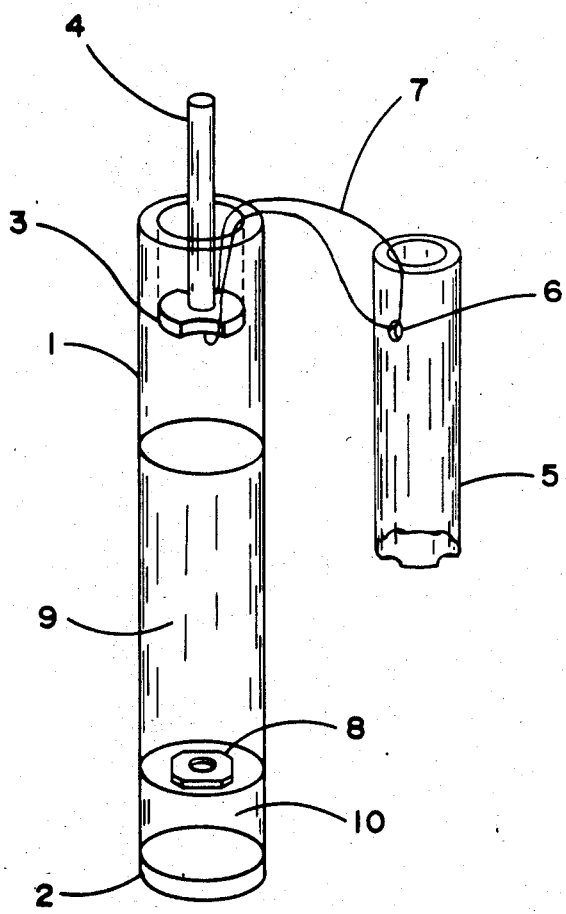
FIG. 1 shows the aviation fuel tester in the "prong" mode with the removable attachment off the fuel receptacle.

Referring more particularly to FIG. 1, it is seen that the aviation fuel tester has a transparent tubular plastic body 1, which is closed at the bottom end by a plastic disk 2 that has been glued to the body 1. The top of the tubular body 1 is partially closed by a plastic disk 3 into which partially circular shaped vents have been cut. The disk 3 is glued to the inner diameter wall of the tubular body 1, at a position recessed from the top edge of the tubular body 1. The plastic parts of the fuel tester are made from extruded acrylic plastic.

A circular well has been cut into the disk 3 and a cylindrical metal prong 4 has been glued into said well in disk 3. The metal prong 4 is made of soft steel. A length of thin fish line 7 has been tied in a loop around the disk 3 and through a hole 6 in the removable attachment 5 so that when the attachment 5 is not actually being used, it will not get lost. The fish line 7 is made of 10 lb. test fish line. The function of the attachment 5 will be described shortly.

Inside the tubular body 1 and kept there by the disks 2 and 3, is a freely movable octagon shaped wafer 8 with a hole in the center.

Preferred numerical dimensions for the aviation fuel tester are as follows. The tubular plastic body 1 has a ¾ in. inner diameter, a ⅛ in. thick wall, and a 1 in. outer diameter. The removable attachment 5 has a ⅝ in. inner diameter, a 1/16 in. thick wall, and a ¾ in. outer diameter. The octagon shaped wafer 8 is 3/16 in. thick, the hole being 3/16 in. in diameter, and the circumscribed diameter of the float as a whole being less than ¾ in. The tubular plastic body 1 has a length of 5 13/16 in. and the attachment 5 has a length of 2½ in. The plastic disk 2 has a 1 in. diameter and is ⅛ in. thick. The vented disk 3 has a ¾ in. diameter and is 3/16 in. thick.

In the "prong" mode of operation, which is shown in FIG. 1, the aviation fuel tester works as follows: The user grasps the tubular body 1 in his hand and approaches a quick-release valve on the wing fuel tank of an airplane such as the Cessna 152 or the Cessna 172. The prong 4 is pressed against the circular valve of the tank, thereby releasing a sample of aviation fuel through the vents of disk 3 into the tubular body 1.

Typical aviation fuel, such as 100 octane low lead fuel, has a density of 0.713–0.796 g/cc. Water has a density of 1.00 g/cc. The float 8, being made of polyethylene, has a density of 0.94–0.96 g/cc. As a result of these densities, the following situation will occur: If there is any water in the fuel sample, the water will form a separate phase 10 at the bottom of the tubular body 1. The gasoline will form a separate phase 9 on top of the water 10. The float 8 will sit at the interface between the water 10 and the gasoline 9, thereby constituting a strongly visible indicator of the location of such a gasoline-water interface.

If there is no water in the fuel mix, then the float 8 will rest on the bottom of the tubular body 1, actually sitting on top of the disk 2.

The float 8 is octagon shaped because it will be less prone to stick to the inner walls of the tubular body 1 than if the float were, say, circular shaped. The float 8 also has a hole in its center for the purpose of avoiding the possibility that a bubble of gasoline might become trapped under the float 8 or the possibility that a bubble of water might be trapped over the float 8.

After visual inspection of the fuel has been completed, the user simply points the top of the tester downward, pours out the fuel, and lets the tester air dry.

Figure 2:
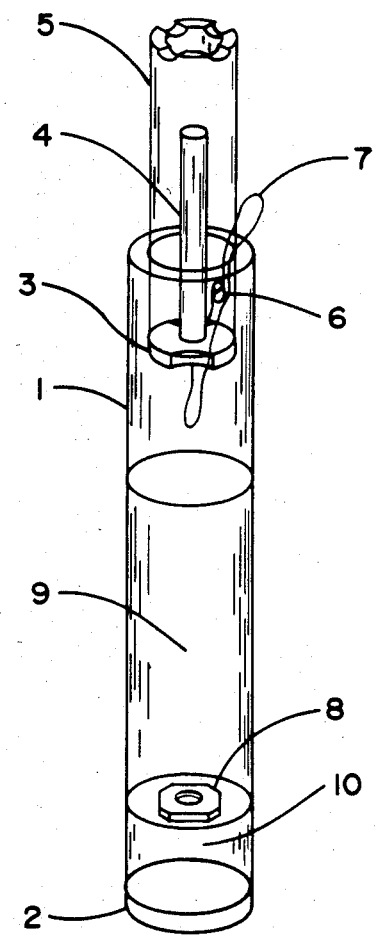
FIG. 2 shows the aviation fuel tester in the "groove" mode with the removable attachment in place on the fuel receptacle.

In the "groove" mode of operation, which is shown in FIG. 2, the aviation fuel tester works as follows: The plastic tubular attachment 5 is placed in the recessed end of the tubular body 1 so as to sit somewhat snugly on top of the vented disk 3. The user grasps the tubular body 1 in his hand and approaches the quick-release valve on the wing fuel tank of an airplane such as the Piper Cherokee, the Piper Warrior, or the Piper Archer. The opposed grooves or indentations on the top of attachment 5 are pressed against the opposed arms of a wing-valve, thereby releasing a sample of fuel through the attachment 5, and through the vents of disk 3, into the tubular body 1. Thereafter, the operation of the fuel water is identical to that described for FIG. 1 above.

It should be noted that although the walls of the tubular body 1 have a definite thickness, because of the effect of refraction, the liquid phases 9 and 10 in FIG. 1 and FIG. 2 appear to extend right up to the outer surface of the tubular body 1. This optical refraction effect is familiar to anyone who has studied the appearance of water in a glass. Thus, there should be no confusion about the fact that the vented disk 3 is indeed glued to the inner diameter wall of the clear tubular body 1 even though the disk 3 may appear to be suspended in air in FIG. 1 and FIG. 2.

The preferred embodiment of the invention shown in FIG. 1 and FIG. 2 should not be taken as a limitation upon the scope of the invention as it is evident that a number of materials and parameters of the disclosed invention may be altered without affecting the scope of the present invention.

What is claimed is:

1. An aviation fuel tester comprising: a hand-held container for receiving a sample of fuel from an airplane fuel tank, said container possessing an attached prong made of soft steel metal, and also possessing a removable attachment with a plurality of diametrically opposed indentations, said container and attachment being made of extruded clear acrylic plastic and thus transparent to allow visualization of the aviation fuel received therein, said tester possessing a string means made of a length of 10 lb. test fish line tied to form a loop tying the said removable attachment to the said container, said container being tubular and closed at one end, the other end of said container possessing a disk coaxially mounted inside the container in a recessed position, said disk possessing drain vents, thereby allowing communication of received aviation fuel between the open end of said container and the container interior, said disk forming a base containing a well into which the said prong is securely and permanently attached in a coaxial orientation, said disk also simultaneously preventing exit from the container of a float container therein, said float being made of polyethylene of density 0.94–0.96 g/cc so as to sit at a gasoline-water interface.

2. An aviation fuel tester as described in claim 1 wherein the removable attachment is tubular and open at both ends, one end of said attachment possessing four diametrically opposed indentations, said attachment being of a size to allow insertion into the recessed opening of said container whereupon said attachment sits on top of said vented disk, thereby allowing communication of received aviation fuel between open indented end of said attachment and the container interior.

3. An aviation fuel tester as described in claim 2 wherein the container is closed at one end by possessing an acrylic plastic disk glued to said end of said container, and the vented, recessed disk is made of acrylic plastic and securely glued to the inner diameter wall of said container.

4. An aviation fuel tester as described in claim 3 wherein the container has a ¾ in. inner diameter, a ⅛ in. thick wall, and a 1 in. outer diameter; the attachment has a ⅝ in. inner diameter, a 1/16 in. thick wall, and a ¾ in. outer diameter; the prong has a 1⅜ in. length and a ⅛ in. diameter; the float is an octagon shaped wafer with a hole in the center, said float being 3/16 in. thick, the hole being 3/16 in. in diameter, and the circumscribed diameter of the float as a whole being less than ¾ in.; the container has a 5 13/16 in. length; the attachment has a 2½ in. length; the disk closing the end of the container has a 1 in. diameter and is ⅛ in. thick; and the vented disk has a ¾ in. diameter and is 3/16 in. thick.

* * * * *